(12) United States Patent
Buyda et al.

(10) Patent No.: US 11,278,316 B2
(45) Date of Patent: Mar. 22, 2022

(54) CLIP COLLAR ADVANCED FIXATION

(71) Applicant: Covidien LP, Mansfield, MA (US)

(72) Inventors: Oksana Buyda, East Haven, CT (US); Anthony Sgroi, Jr., Wallingford, CT (US); Christopher Tokarz, Torrington, CT (US)

(73) Assignee: COVIDIEN LP, Mansfield, MA (US)

( * ) Notice: Subject to any disclaimer, the term of this patent is extended or adjusted under 35 U.S.C. 154(b) by 0 days.

(21) Appl. No.: 16/403,767

(22) Filed: May 6, 2019

(65) Prior Publication Data

US 2019/0254704 A1    Aug. 22, 2019

Related U.S. Application Data

(62) Division of application No. 15/432,227, filed on Feb. 14, 2017, now Pat. No. 10,327,809.

(60) Provisional application No. 62/301,222, filed on Feb. 29, 2016, provisional application No. 62/301,235, filed on Feb. 29, 2016.

(51) Int. Cl.
*A61B 17/34* (2006.01)
*A61B 17/00* (2006.01)
*A61B 34/35* (2016.01)

(52) U.S. Cl.
CPC .... *A61B 17/3423* (2013.01); *A61B 17/00234* (2013.01); *A61B 17/3421* (2013.01); *A61B 34/35* (2016.02); *A61B 2017/347* (2013.01); *A61B 2017/3419* (2013.01); *A61B 2017/3492* (2013.01)

(58) Field of Classification Search
CPC ...... A61B 2017/347; A61B 2017/3419; A61B 2017/3492; A61M 2025/024
See application file for complete search history.

(56) References Cited

U.S. PATENT DOCUMENTS

| 84,448 A | 11/1868 | Watson et al. |
| 1,579,719 A | 4/1926 | Lavender |
| 3,468,318 A | 9/1969 | Cook |
| 3,570,498 A | 3/1971 | Weighton |

(Continued)

FOREIGN PATENT DOCUMENTS

| CA | 2901425 A1 * | 9/2014 | ......... A61B 17/3417 |
| FR | 2734161 A1 | 11/1996 | |

(Continued)

OTHER PUBLICATIONS

Extended European Search Report issued in European Application No. EP11250291 dated Jun. 24, 2011.

(Continued)

*Primary Examiner* — Jan Christopher L Merene
(74) *Attorney, Agent, or Firm* — Carter, DeLuca & Farrell LLP

(57) ABSTRACT

A collar for a surgical access device includes an annular body laterally attachable to a cannula of the surgical access device. A spring is coupled to the annular body and movable between an uncompressed state and a compressed state. The spring is configured to manipulate the annular body between a first condition and a second condition to selectively fix the annular body at predetermined locations along the cannula or to laterally remove the annular body from the cannula while the cannula is supported within a patient's body.

20 Claims, 14 Drawing Sheets

(56) References Cited

U.S. PATENT DOCUMENTS

| | | | |
|---|---|---|---|
| 3,807,393 A | 4/1974 | McDonald | |
| 4,393,873 A | 7/1983 | Nawash et al. | |
| 4,471,512 A | 9/1984 | Thalenfeld | |
| 4,601,710 A | 7/1986 | Moll | |
| 4,608,965 A | 9/1986 | Anspach, Jr. et al. | |
| 4,654,030 A | 3/1987 | Moll et al. | |
| 4,846,784 A | 7/1989 | Haber | |
| 5,002,557 A | 3/1991 | Hasson | |
| 5,030,206 A | 7/1991 | Lander | |
| 5,073,169 A | 12/1991 | Raiken | |
| 5,104,382 A | 4/1992 | Brinkerhoff et al. | |
| 5,119,665 A * | 6/1992 | Stafford | B25B 7/02 72/409.13 |
| 5,122,122 A | 6/1992 | Allgood | |
| 5,137,520 A | 8/1992 | Maxson et al. | |
| 5,147,316 A | 9/1992 | Castillenti | |
| 5,176,697 A | 1/1993 | Hasson et al. | |
| 5,183,033 A | 2/1993 | Wilk | |
| 5,203,773 A | 4/1993 | Green | |
| 5,215,531 A | 6/1993 | Maxson et al. | |
| 5,217,451 A | 6/1993 | Freitas | |
| 5,232,440 A | 8/1993 | Wilk | |
| 5,232,451 A | 8/1993 | Freitas et al. | |
| 5,248,302 A | 9/1993 | Patrick et al. | |
| 5,257,975 A | 11/1993 | Foshee | |
| 5,267,970 A | 12/1993 | Chin et al. | |
| 5,279,564 A | 1/1994 | Taylor | |
| 5,279,575 A | 1/1994 | Sugarbaker | |
| 5,282,788 A | 2/1994 | Wilk et al. | |
| 5,290,243 A | 3/1994 | Chodorow et al. | |
| 5,290,249 A | 3/1994 | Foster et al. | |
| 5,312,354 A | 5/1994 | Allen et al. | |
| 5,318,012 A | 6/1994 | Wilk | |
| 5,318,580 A | 6/1994 | Gresl, Jr. | |
| 5,330,497 A | 7/1994 | Freitas et al. | |
| 5,345,927 A | 9/1994 | Bonutti | |
| 5,354,283 A | 10/1994 | Bark et al. | |
| 5,387,196 A | 2/1995 | Green et al. | |
| 5,387,197 A | 2/1995 | Smith et al. | |
| 5,439,476 A | 8/1995 | Frantzides | |
| 5,486,190 A | 1/1996 | Green | |
| 5,540,711 A | 7/1996 | Kieturakis et al. | |
| 5,637,097 A | 6/1997 | Yoon | |
| 5,681,340 A | 10/1997 | Veronikis | |
| 5,685,856 A | 11/1997 | Lehrer | |
| 5,713,869 A | 2/1998 | Morejon | |
| 5,782,813 A | 7/1998 | Yoon | |
| 5,792,112 A | 8/1998 | Hart et al. | |
| 5,836,913 A | 11/1998 | Orth et al. | |
| 5,857,999 A | 1/1999 | Quick et al. | |
| 5,868,699 A | 2/1999 | Woodruff et al. | |
| 5,925,058 A | 7/1999 | Smith et al. | |
| 5,935,107 A | 8/1999 | Taylor et al. | |
| 5,941,898 A | 8/1999 | Moenning et al. | |
| 5,951,588 A | 9/1999 | Moenning | |
| 5,957,888 A | 9/1999 | Hinchliffe | |
| 5,971,960 A | 10/1999 | Flom et al. | |
| 6,016,595 A | 1/2000 | Dysarz | |
| 6,056,689 A | 5/2000 | Lenox et al. | |
| 6,059,816 A | 5/2000 | Moenning | |
| 6,086,603 A | 7/2000 | Termin et al. | |
| 6,171,319 B1 | 1/2001 | Nobles et al. | |
| 6,254,271 B1 | 7/2001 | Lin | |
| 6,270,484 B1 | 8/2001 | Yoon | |
| 6,270,490 B1 | 8/2001 | Hahnen | |
| 6,355,028 B2 | 3/2002 | Castaneda et al. | |
| 6,432,085 B1 | 8/2002 | Stellon et al. | |
| 6,451,041 B1 | 9/2002 | Moenning et al. | |
| 6,464,690 B1 | 10/2002 | Castaneda et al. | |
| 6,464,691 B1 | 10/2002 | Castaneda et al. | |
| 6,485,476 B1 | 11/2002 | von Dyck et al. | |
| 6,503,245 B2 | 1/2003 | Palmer et al. | |
| 6,524,283 B1 | 2/2003 | Hopper et al. | |
| 6,551,303 B1 | 4/2003 | Van Tassel et al. | |
| 6,582,420 B2 | 6/2003 | Castaneda et al. | |
| 6,592,573 B2 | 7/2003 | Castaneda et al. | |
| 6,620,129 B2 | 9/2003 | Stecker et al. | |
| 6,632,197 B2 | 10/2003 | Lyon | |
| 6,652,555 B1 | 11/2003 | VanTassel et al. | |
| 6,652,556 B1 | 11/2003 | VanTassel et al. | |
| 6,676,665 B2 | 1/2004 | Foley et al. | |
| 6,689,150 B1 | 2/2004 | VanTassel et al. | |
| 6,695,816 B2 | 2/2004 | Cassidy, Jr. | |
| 6,730,108 B2 | 5/2004 | Van Tassel et al. | |
| 6,773,418 B1 | 8/2004 | Sharrow et al. | |
| 6,908,454 B2 | 6/2005 | McFarlane | |
| 6,941,169 B2 | 9/2005 | Pappu | |
| 6,949,113 B2 | 9/2005 | Van Tassel et al. | |
| 7,001,333 B2 | 2/2006 | Hamel et al. | |
| 7,011,671 B2 | 3/2006 | Welch | |
| 7,097,648 B1 | 8/2006 | Globerman et al. | |
| 7,125,411 B2 | 10/2006 | Guanche | |
| 7,169,164 B2 | 1/2007 | Borillo et al. | |
| 7,235,064 B2 | 6/2007 | Hopper et al. | |
| 7,300,448 B2 | 11/2007 | Criscuolo et al. | |
| 7,377,897 B1 | 5/2008 | Kunkel et al. | |
| 7,419,496 B2 | 9/2008 | Staudner | |
| 7,549,983 B2 | 6/2009 | Roue et al. | |
| 7,621,950 B1 | 11/2009 | Globerman et al. | |
| 7,641,664 B2 | 1/2010 | Pagano | |
| 7,691,089 B2 | 4/2010 | Gresham | |
| 7,722,641 B2 | 5/2010 | van der Burg et al. | |
| 7,727,189 B2 | 6/2010 | VanTassel et al. | |
| 7,798,998 B2 | 9/2010 | Thompson et al. | |
| 7,824,327 B2 | 11/2010 | Smith | |
| 7,854,450 B2 | 12/2010 | Takagi | |
| 7,922,656 B2 | 4/2011 | Beckman et al. | |
| 7,959,610 B2 | 6/2011 | Elbert et al. | |
| 7,988,669 B2 | 8/2011 | Hathaway et al. | |
| 8,062,305 B2 | 11/2011 | Wenchell | |
| 8,147,453 B2 | 4/2012 | Albrecht et al. | |
| 8,157,833 B2 | 4/2012 | Au et al. | |
| 8,162,893 B2 | 4/2012 | Okihisa et al. | |
| 8,221,317 B2 | 7/2012 | Maynard et al. | |
| 8,480,575 B2 | 7/2013 | Albrecht et al. | |
| 10,327,809 B2 | 6/2019 | Buyda et al. | |
| 2002/0111537 A1 | 8/2002 | Taylor et al. | |
| 2003/0144629 A1 | 7/2003 | Hawk et al. | |
| 2003/0153926 A1 | 8/2003 | Schmieding et al. | |
| 2004/0138702 A1 | 7/2004 | Peartree et al. | |
| 2005/0065410 A1 | 3/2005 | Bjork et al. | |
| 2005/0125021 A1 | 6/2005 | Nance et al. | |
| 2005/0169728 A1 * | 8/2005 | Attanasio | B64C 1/12 411/352 |
| 2005/0203467 A1 | 9/2005 | O'Heeron et al. | |
| 2005/0209608 A1 | 9/2005 | O'Heeron | |
| 2005/0288634 A1 | 12/2005 | O'Heeron et al. | |
| 2006/0106402 A1 | 5/2006 | McLucas | |
| 2006/0206008 A1 | 9/2006 | Dalton | |
| 2007/0005086 A1 | 1/2007 | Gresham | |
| 2007/0260124 A1 | 11/2007 | Dobrovolny | |
| 2008/0058605 A1 | 3/2008 | Sorensen | |
| 2008/0319268 A1 | 12/2008 | Michaeli et al. | |
| 2009/0093682 A1 | 4/2009 | Izzo et al. | |
| 2009/0149857 A1 | 6/2009 | Culbert et al. | |
| 2009/0182282 A1 * | 7/2009 | Okihisa | A61B 17/3423 604/165.01 |
| 2010/0161024 A1 | 6/2010 | Kennedy, II et al. | |
| 2010/0249709 A1 | 9/2010 | Fischvogt | |
| 2010/0312068 A1 | 12/2010 | Dalton | |
| 2011/0144440 A1 | 6/2011 | Cropper et al. | |
| 2011/0160538 A1 | 6/2011 | Ravikumar et al. | |
| 2011/0190592 A1 | 8/2011 | Kahle et al. | |
| 2011/0196205 A1 | 8/2011 | Hathaway et al. | |
| 2011/0263945 A1 | 10/2011 | Peterson et al. | |
| 2014/0066953 A1 * | 3/2014 | Keating | A61B 17/3423 606/130 |
| 2014/0171946 A1 * | 6/2014 | Benson | A61B 17/17 606/79 |

(56) References Cited

U.S. PATENT DOCUMENTS

2015/0045623 A1    2/2015   Fischvogt
2018/0206883 A1    7/2018   McIntyre

FOREIGN PATENT DOCUMENTS

| JP | H06509485 A | 10/1994 |
| JP | 2004057520 A | 2/2004 |
| JP | 2010500059 A | 1/2010 |
| WO | 9219298 A1 | 11/1992 |
| WO | 0234164 A2 | 5/2002 |
| WO | 02096307 A2 | 12/2002 |
| WO | 2008109408 A2 | 9/2008 |

OTHER PUBLICATIONS

Extended European Search Report issued in corresponding European Application No. 17158237.2 dated May 12, 2017.
Australian Examination Report for application No. 2017201176 dated Nov. 26, 2020.
Japanese Office Action for application No. 2017-033597 dated Dec. 11, 2020 with English translation.
Chinese Office Action for application No. 201710113026.0 dated Sep. 30, 2020 with English translation.

* cited by examiner

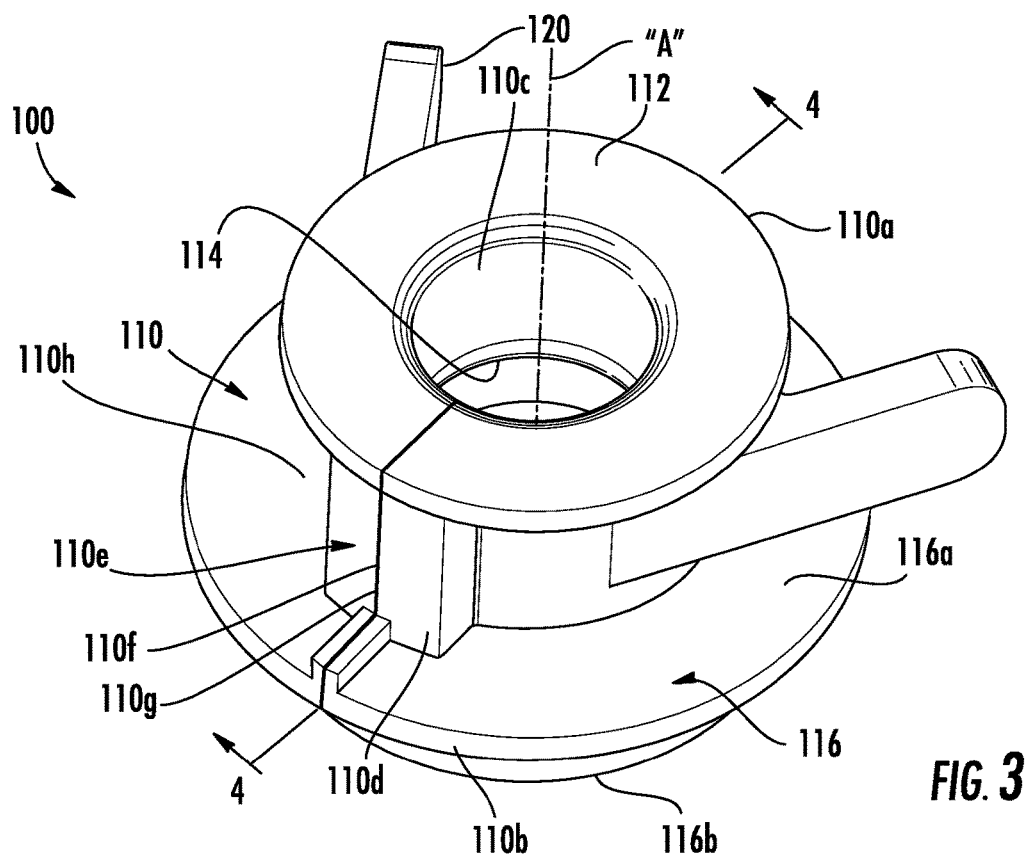
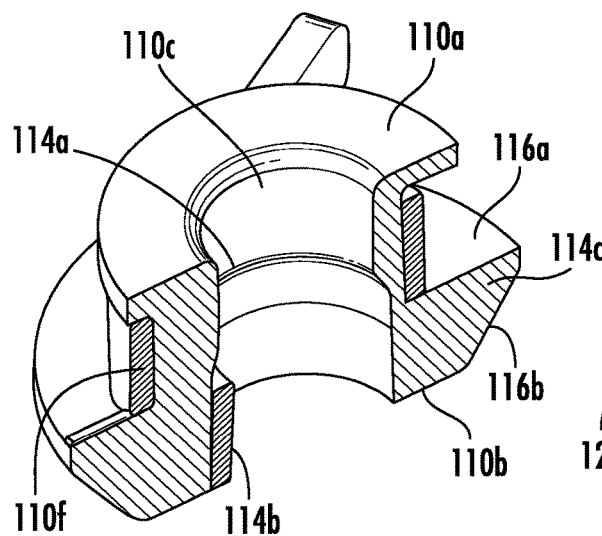
FIG. 4
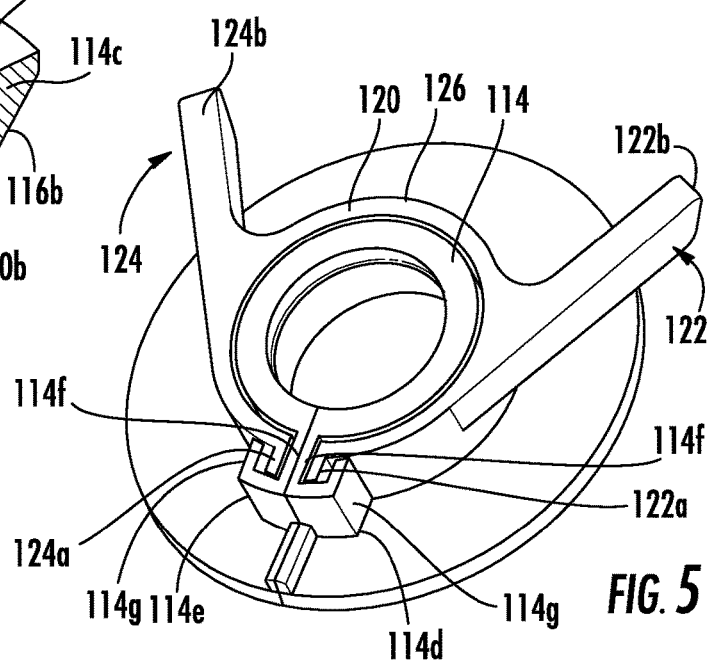
FIG. 5

CLIP COLLAR ADVANCED FIXATION

CROSS REFERENCE TO RELATED APPLICATIONS

This application is a divisional of U.S. patent application Ser. No. 15/432,227 filed Feb. 14, 2017, which claims the benefit of and priority to U.S. Provisional Patent Application Ser. No. 62/301,222 filed Feb. 29, 2016 and U.S. Provisional Patent Application Ser. No. 62/301,235 filed Feb. 29, 2016, the entire contents of each of which are incorporated by reference herein.

TECHNICAL FIELD

This disclosure relates to surgical access and, more particularly, to collars for surgical access devices that facilitate surgical access in a minimally invasive surgical procedure.

BACKGROUND

Minimally invasive surgical procedures, including both endoscopic and laparoscopic procedures, enable surgery to be performed on organs, tissues and vessels far removed from an opening through the tissue. Laparoscopic and endoscopic procedures generally require that any instrumentation inserted into the body be sealed, i.e., provisions must be made to ensure that gases do not enter or exit the body through the incision as, for example, in surgical procedures in which the surgical region is insufflated. These procedures typically employ surgical instruments which are introduced into the body through a cannula. The cannula has a housing at a proximal end thereof in which a seal assembly is mounted. The seal assembly provides a substantially fluid tight seal about the instrument to preserve the integrity of the established pneumoperitoneum.

While minimally invasive procedures have several advantages over traditional open surgery, including less patient trauma, reduced recovery time, reduced potential for infection, etc., such procedures are not without risk and challenge. Accordingly, there is a continuing need for providing improved apparatus that can be utilized for enhancing efficiencies and effectiveness of these procedures.

SUMMARY

According to one aspect of the present disclosure, a surgical access system is provided. The surgical access system includes a collar and a surgical access device having a housing and a cannula extending from the housing. According to another aspect of the present disclosure, a collar for a surgical access device is provided.

The collar includes a spring and an annular body laterally attachable to the cannula. The spring is coupled to the annular body and movable between an uncompressed state and a compressed state. The spring is configured to manipulate the annular body between a first condition and a second condition to selectively fix the annular body at predetermined locations along the cannula or to laterally remove the annular body from the cannula while the cannula is supported within a patient's body. Movement of the spring from the compressed state to the uncompressed state may enable the annular body to frictionally secure to the cannula. The spring may include opposed arms that pivot relative to one another as the spring moves between the uncompressed and compressed states. One or both of the opposed arms may include a restraining member that prevents over-compression of the opposed arms. Each of the opposed arms may include a leading end and a trailing end. As the spring moves toward the compressed state, the trailing ends may move toward one another and the leading ends may move away from one another.

In some embodiments, the annular body may include opposed end faces disposed in mirrored relation and positioned to define a vertical slit through the annular body. The vertical slit may be arranged to enable the annular body to separate and expose a central passage extending through the annular body as the spring moves toward the compressed state.

In certain embodiments, as the spring moves toward the uncompressed state, the trailing ends may move away from one another and the leading ends may move toward one another such that opposed end faces approximate one another and the annular body encloses the central passage.

In some embodiments, the annular body may include a distal portion having a conical configuration.

In certain embodiments, the annular body may be formed of a flexible material. The annular body may include soft rubber material.

According to yet another aspect of the present disclosure, a surgical access system includes a collar and a surgical access device having a housing and a cannula extending from the housing. The cannula defines a longitudinal axis.

The collar includes an annular body defining a passage therethrough. The passage is configured to receive the cannula therethrough. The annular body may be selectively securable to the cannula at a first axial location along the cannula. The annular body may be selectively securable to the cannula at a second axial location along the cannula in response to relative axial movement between the cannula and the annular body.

A spring is mounted to the annular body. The spring is movable between an uncompressed state and a compressed state. The spring may be configured to prevent relative axial movement between the annular body and the cannula while the annular body is mounted on the cannula at one of the first and second axial locations and the spring is in the uncompressed state. The spring may be configured to enlarge the passage and enable relative axial movement between the cannula and annular body as the spring moves from the uncompressed state to the compressed state.

In some embodiments, movement of the spring from the compressed state to the uncompressed state enables the annular body to frictionally secure to the cannula at one of the first and second axial locations along the cannula.

In certain embodiment, the spring may be integrally formed with the annular body.

In some embodiments, the annular body may include a distal portion having conical configuration. The distal portion may include a ledge at a proximal end thereof. The distal portion may taper distally from the ledge to a distal end of the distal portion. The annular body may include a tubular portion that extends proximally from the distal portion. The spring may be coupled to the tubular portion and wherein movement of the spring between the compressed and uncompressed states may move the tubular portion radially relative to the longitudinal axis and may change dimensions of the passage.

In certain embodiments, a plurality of tabs may extend between the spring and the annular body to couple the spring to the annular body.

In some embodiments, the spring includes a mounting portion and a flexible portion. The flexible portion may be compressible toward the longitudinal axis to draw the mounting portion away from the longitudinal axis.

Advantageously, embodiments of the present disclosure provide cannula fixation for minimizing the risk of unintentional axial displacement (e.g., trocar push-in and/or pull-out). Even while providing axial fixation, embodiments of the presently disclosed devices may also enable articulation of the surgical access devices for changing or adjusting orientations of the surgical access devices or instruments advanced therethrough. In addition, such cannula fixation promotes seal integrity and helps limit loss of insufflation fluids during laparoscopic procedures, thereby facilitating maintenance of the pneumoperitoneum. Further, selective attachment/detachment of embodiments of the presently disclosed collars provides clinicians with increased usability, convenience, and a means to improve efficiencies and effectiveness of surgical procedures. Further still, embodiments of the present disclosure provide the convenience of being operated with one hand.

Other aspects, features, and advantages will be apparent from the description, the drawings, and the claims that follow.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein:

FIG. 3 is a perspective view of the collar of the surgical access system of FIGS. 1 and 2;

FIG. 4 is a perspective, cross-sectional view of the collar of FIG. 3 as taken along line 4-4 shown in FIG. 3;

FIG. 5 is a perspective view of the collar of FIG. 3 with portions of the collar removed for clarity;

DETAILED DESCRIPTION

Figure 1:
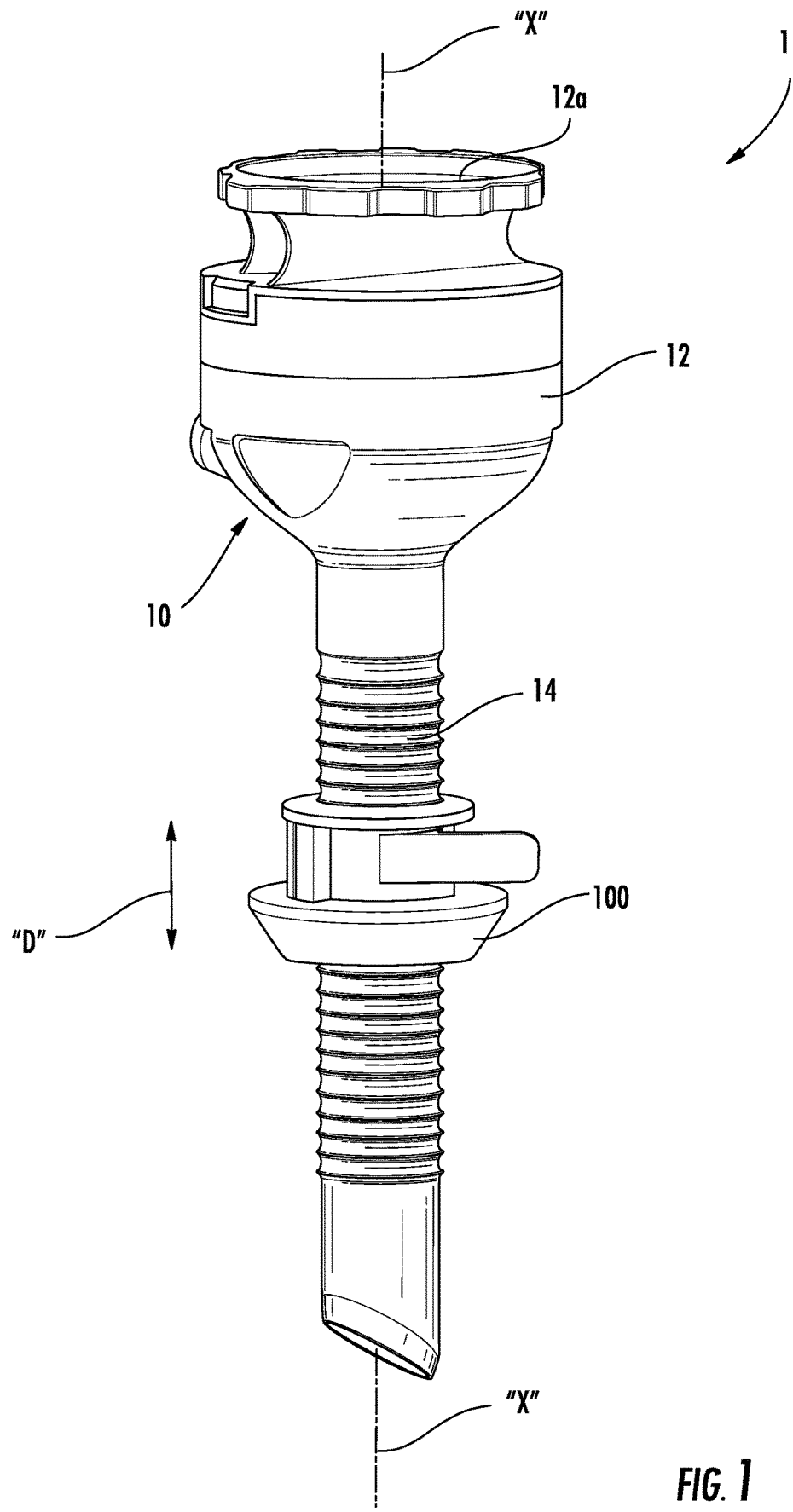
FIG. 1 is a perspective view of one embodiment of a surgical access system with one embodiment of a collar of the surgical access system positioned at a first axial location along a surgical access device of the surgical access system.

Particular embodiments of the present disclosure are described hereinbelow with reference to the accompanying drawings in which like reference numerals designate identical or corresponding elements in each of the several views. As used herein, the term "distal" refers to that portion of the system, device, and/or component(s) thereof, which is farther from the user, while the term "proximal" refers to that portion of the system, device, and/or component(s) thereof, which is closer to the user. As used herein, the term "clinician" refers to a doctor, nurse, or other care provider and may include support personnel. In the following description, well-known functions or constructions are not described in detail to avoid obscuring the present disclosure in unnecessary detail.

Figure 2:
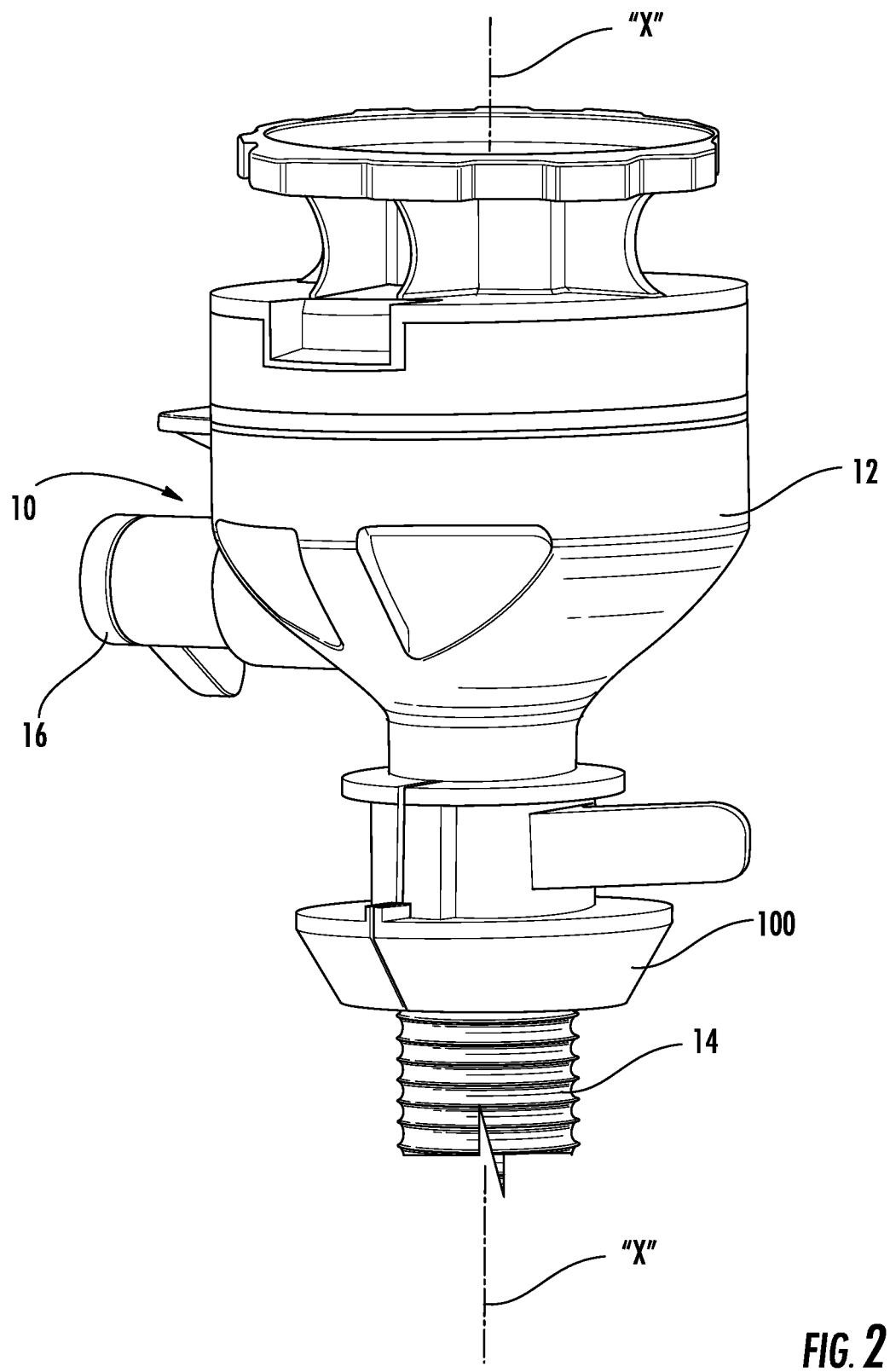
FIG. 2 is a perspective view of the surgical access system of FIG. 1 with the collar thereof positioned at a second axial location along the surgical access device thereof.

Turning now to FIGS. 1 and 2, one embodiment of a surgical access system, generally referred to as surgical access system 1, includes a surgical access device 10 and a collar 100 that is selectively mountable to the surgical access device 10.

The surgical access device 10 of the surgical access system 1 can include any apparatus suitable for introduction, typically utilizing a trocar, and passage of surgical objects into underlying tissue (e.g., within the abdominal cavity during a laparoscopic surgical procedure) including, e.g., trocar assemblies, endoscopic portals, hand access devices, etc., through an incision or through a natural body opening. The surgical access device 10 can include any suitable cannula or trocar assembly having a housing 12 that supports a seal assembly 12a and a cannula or trocar 14 that extends distally from the housing 12. For example, the surgical access device 10 may include smooth cannulas, ribbed cannulas, balloon cannulas, etc. and may be combined with any suitable obturator (not shown) such as a bladed, bladeless, optical bladeless, VersaStep™, VersaOne™, cone, etc. The surgical access device 10 may further includes valve assembly 16 configured to selectively control fluid flow (e.g., insufflation fluid) through the surgical access device 10.

In general, the surgical access device 10 of the surgical access system 1 functions to provide a substantial seal between a body cavity of a patient and the outside atmosphere before, during, and after insertion of a surgical instrument (not shown) or object through the surgical access device 10. For instance, the seal assembly 12a of the surgical access device 10 may be capable of accommodating surgical instruments of varying diameters (e.g., from 5 mm to 15 mm) by providing a fluid tight seal with each surgical instrument inserted through the seal assembly 12a. The seal assembly 12a may receive various types of instrumentation adapted for insertion through the surgical access device 10 while maintaining a fluid tight interface about the instrumentation to preserve the atmospheric integrity of a surgical procedure from gas and/or fluid leakage. The seal assembly 12a may be configured to accommodate angular manipulation of surgical instruments relative to a longitudinal axis "X" defined by the surgical access device 10. Examples of surgical instruments may include clip appliers, graspers, dissectors, retractors, staplers, laser probes, photographic devices, endoscopes and laparoscopes, tubes, and the like. Such instruments will be collectively referred to herein as "instruments or instrumentation."

For a more detailed description of the construction and operation of surgical access devices, reference may be made to U.S. Patent Application Publication No. 2015/0045623, the entire contents of which are incorporated by reference herein.

With reference to FIGS. 3-5, the collar 100 of the surgical access system 1 includes an annular body 110 and spring 120 coupled to the annular body 110. The annular body 110 of the collar 100 has a proximal end 110a and a distal end 110b. The annular body 110 has an inner surface 110c and an outer surface 110d. A vertical slit 110e is defined through the annular body 110 and extends from the inner surface 110c of the annular body 110 to the outer surface 110d of the annular body 110 and from the proximal end 110a of the annular body 110 to the distal end 110b of the annular body 110 so as to define a pair of opposed end faces 110f, 110g. The inner surface 110c of the annular body 110 defines a central passage 110h through the annular body 110. The central passage 110h extends from the proximal end 110a of the annular body 110 to the distal end 110b of the annular body 110 along a central longitudinal axis "A" of the annular body 110. The annular body 110 includes a flange 112 on the proximal end 110a of the annular body 110. The flange 112 is supported on a proximal end of a tubular portion 114 of the annular body 110.

The tubular portion 114 of the annular body 110 extends distally from the flange 112 to a distal portion 116 of the annular body 110. The tubular portion 114 includes an upper portion 114a having an upper portion diameter, a lower portion 114b having a lower portion diameter, and a transition portion 114c that extends between the upper and lower portions 114a, 114b. The upper portion diameter of the upper portion 114a is smaller than the lower portion diameter of the lower portion 114b such that the transition portion 114c is supported at non-perpendicular angle (e.g., slanted) relative to the upper and/or lower portions 114a, 114b. In some embodiments, the tubular portion 114 may include a single diameter therealong. In certain embodiments, the tubular portion 114 may include any number diameters which may be the same and/or different from one or more of the other diameters of the tubular portion 114. The tubular portion 114 can have any suitable cross-sectional shape including circular and non-circular configurations.

As seen in FIG. 5, the tubular portion 114 of the annular body 110 includes first and second hook members 114d, 114e that extend radially outward from an outer surface of the tubular portion 114 adjacent the vertical slit 110e of the annular body 110. The first and second hook members 114d, 114e of the tubular portion 114 are disposed in mirrored relation. Each of the first and second hook members 114d, 114e includes a divider wall 114f and a hook leg 114g that extends from the divider wall 114f. The divider walls 114f of the first and second hook members 114d, 114e are separated by the vertical slit 110e of the annular body 110 (see FIG. 3).

The distal portion 116 of the annular body 10 includes a ledge 116a and a tapered portion 116b that tapers distally from the ledge 116a to the distal end 110b of the annular body 110. The distal portion 116 is configured to sealing support the collar 100 within a body opening such as an incision or natural orifice (not shown) while enabling the collar 110 to be rotationally and/or articulatably movable relative to the body opening. For example, the collar 110 can be articulated as the surgical access device 10 (and/or any surgical instruments received through the surgical access device 10) supported by the collar 110 is/are articulated to reposition the surgical access device 10 (and/or the surgical instruments) within a body cavity (not shown).

The spring 120 of the collar 100 is supported about the tubular portion 114 of the annular body 110 of the collar 100 between a bottom surface of the flange 112 of the annular body 110 and a top surface of the ledge 116a of the distal portion 116 of the annular body 110. The spring 120 includes first and second arms 122, 124 that are pivotally coupled by a connecting segment 126 and disposed in opposed relation. Inner surfaces of the first and second arms 122, 124 of the connecting segment 126 define an opening 128 that receives an outer surface of the tubular portion 114 of the annular body 110. The first and second arms 122, 124 include leading ends 122a, 124a and trailing ends 122b, 124b, respectively. The leading end 122a of the first arm 122 is mated with the first hook member 114d of the tubular portion 114 and the leading end 124a of the second arm 124 is mated with the second hook member 114e of the tubular portion 114.

Figure 6:
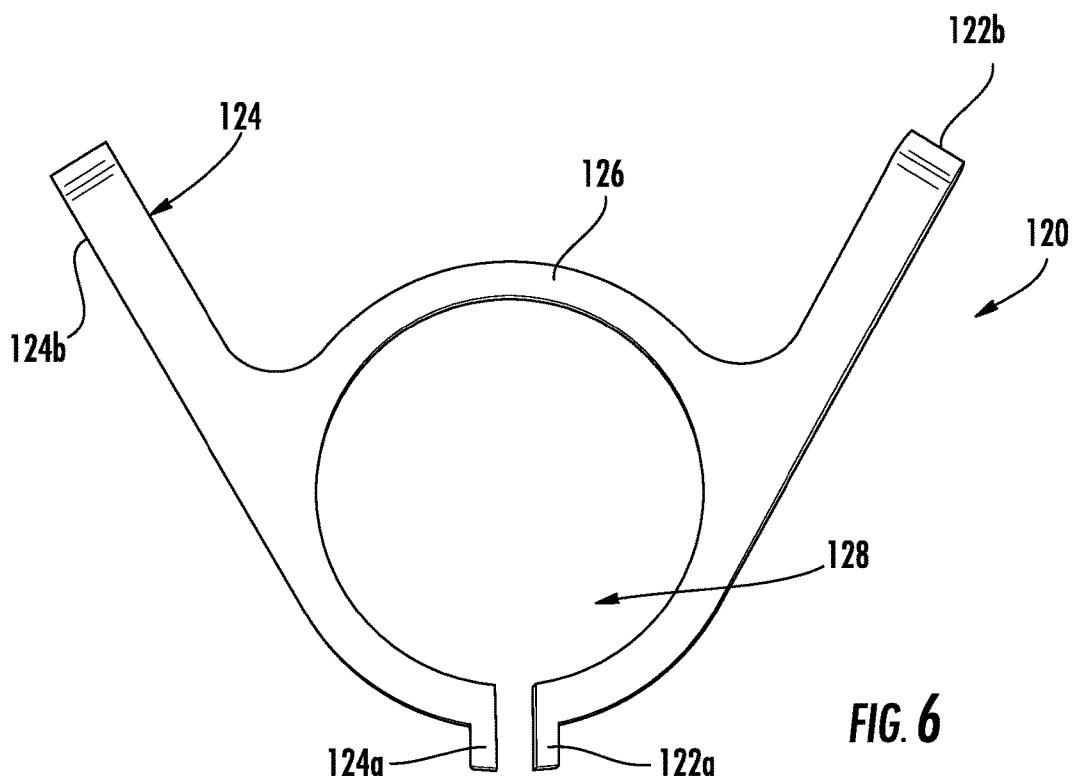
FIGS. 6 and 7 are progressive views of a spring of the collar of FIG. 3, the spring shown positioned in uncompressed and compressed states.
Figure 7:
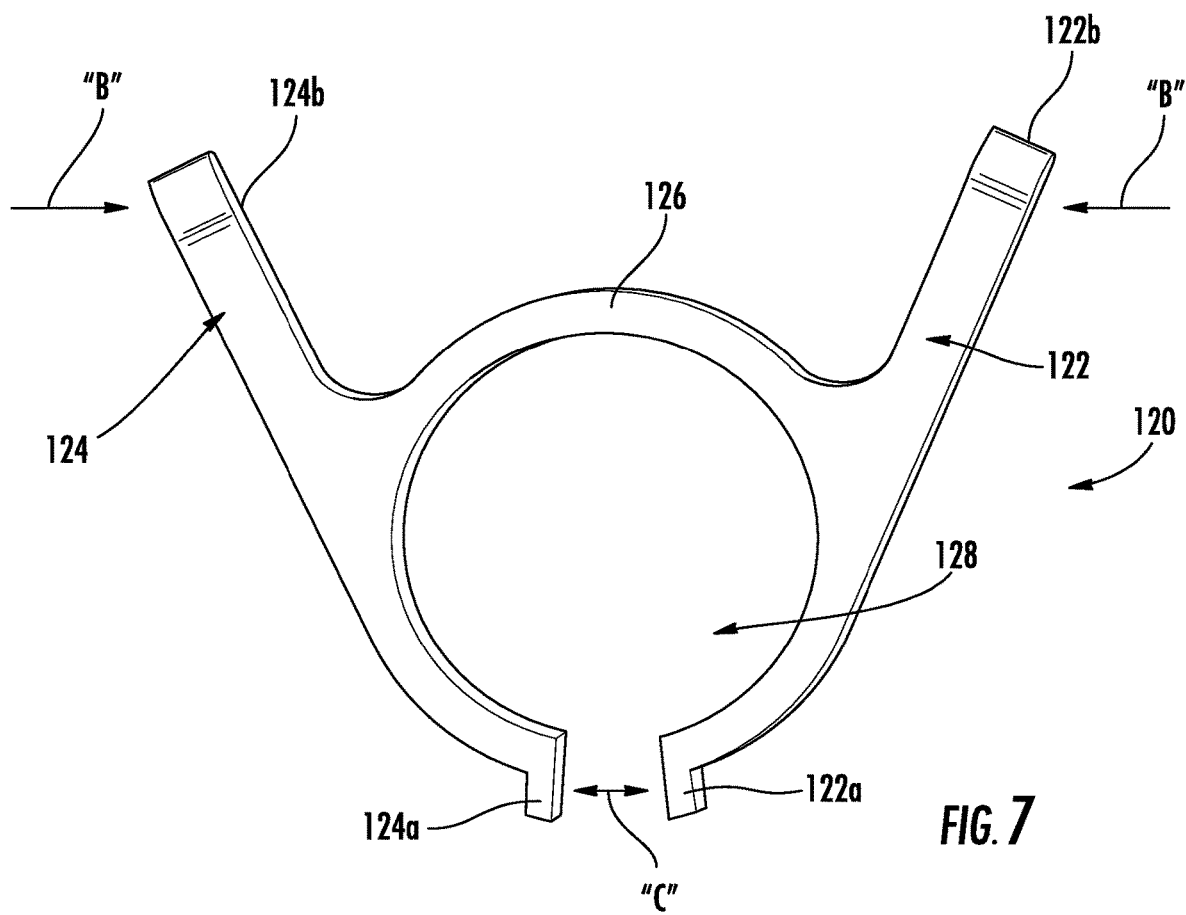
Figure 8:
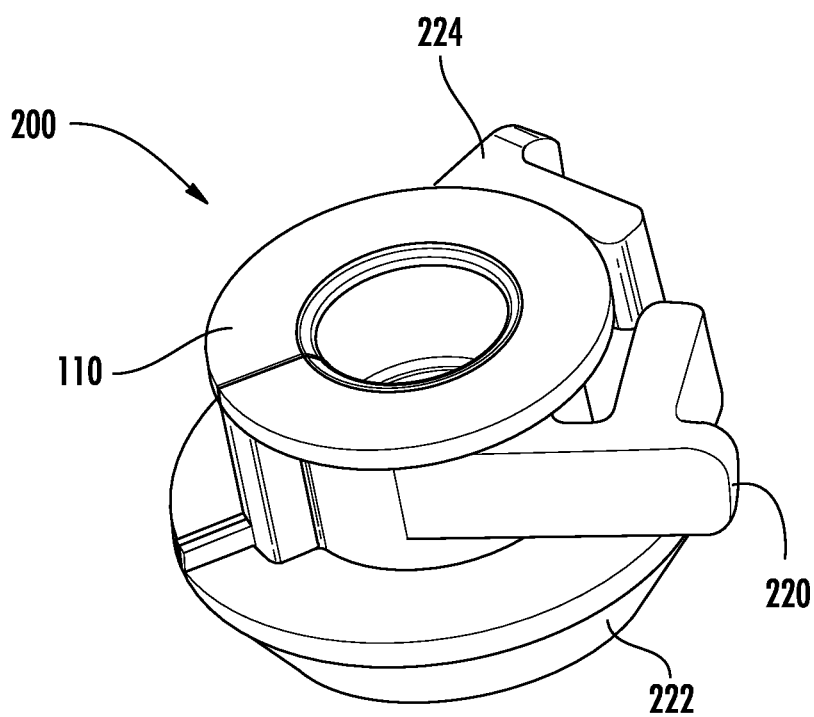
FIG. 8 is a perspective view of another embodiment of a collar.
Figure 9:
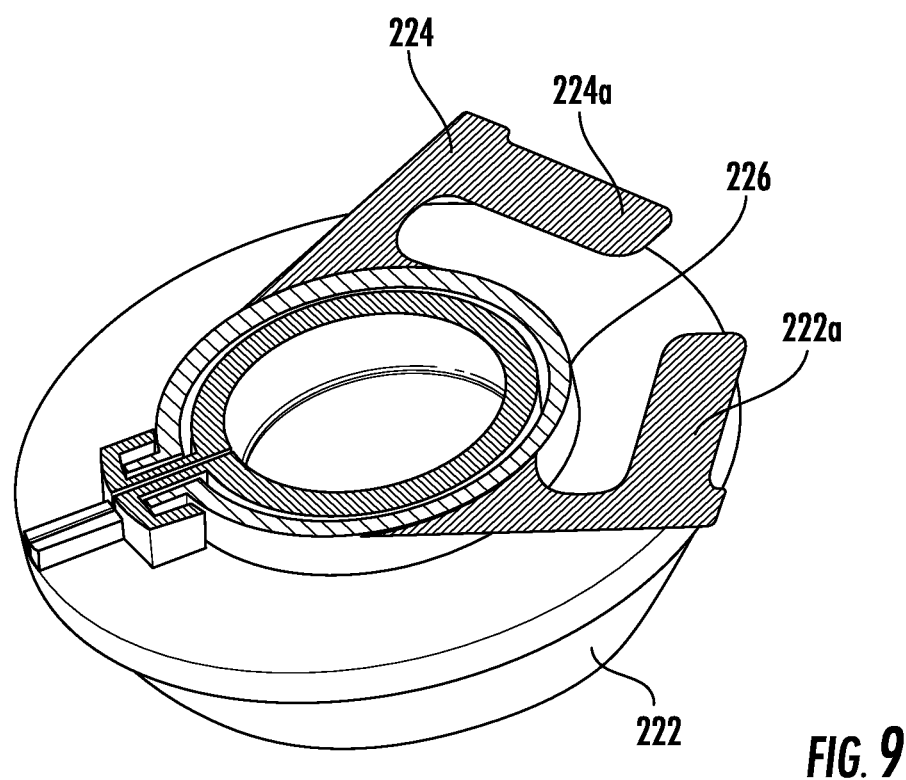
FIG. 9 is a perspective view of the collar of FIG. 8 with a top portion thereof removed for clarity.
Figure 10:
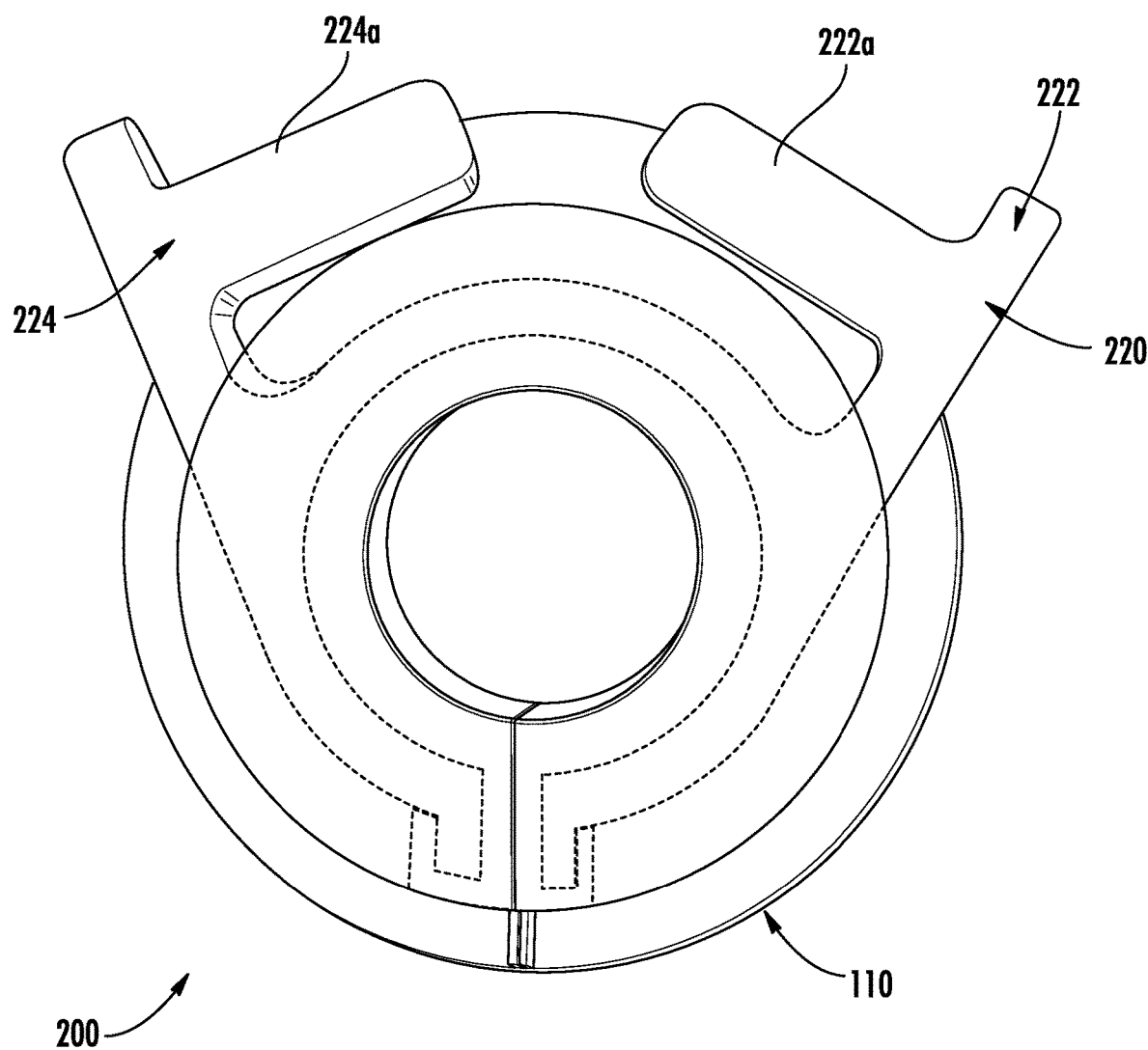
FIGS. 10 and 11 are progressive views of the collar of FIG. 8, the collar shown positioned in uncompressed and compressed states.
Figure 11:
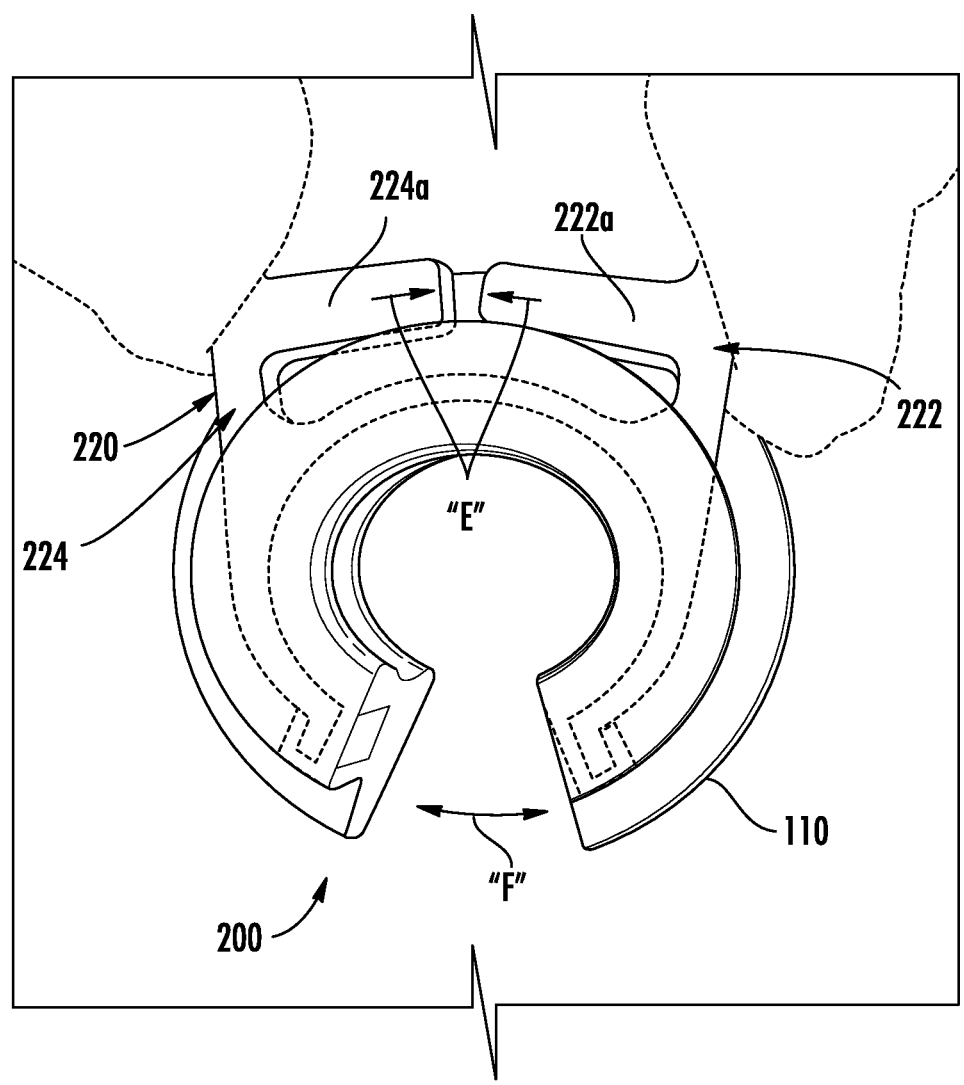
Figure 12:
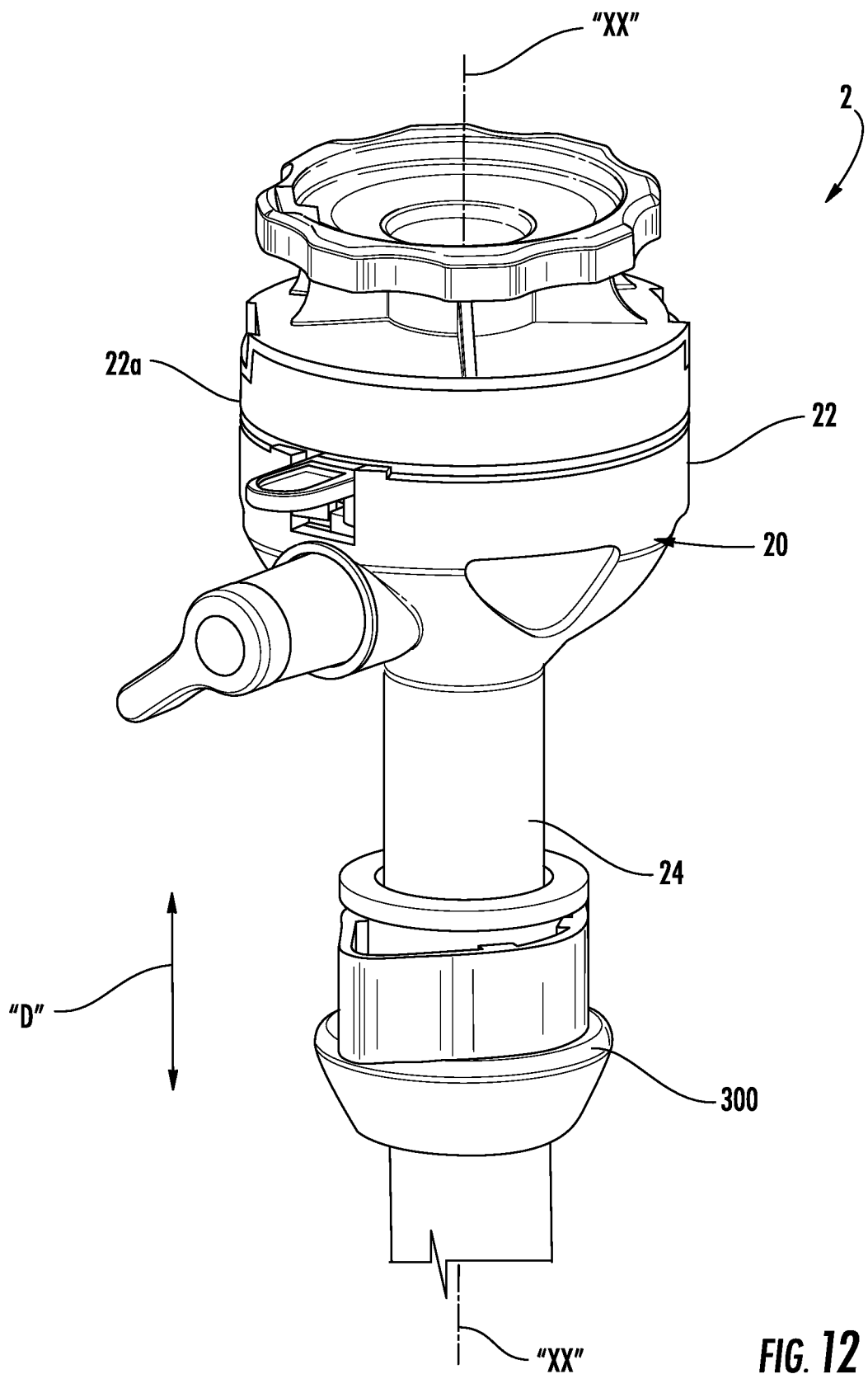
FIG. 12 is a perspective view of another embodiment of a surgical access system with another embodiment of a collar of the surgical access system positioned at first axial location along another embodiment of a surgical access device of the surgical access system.
Figure 13:
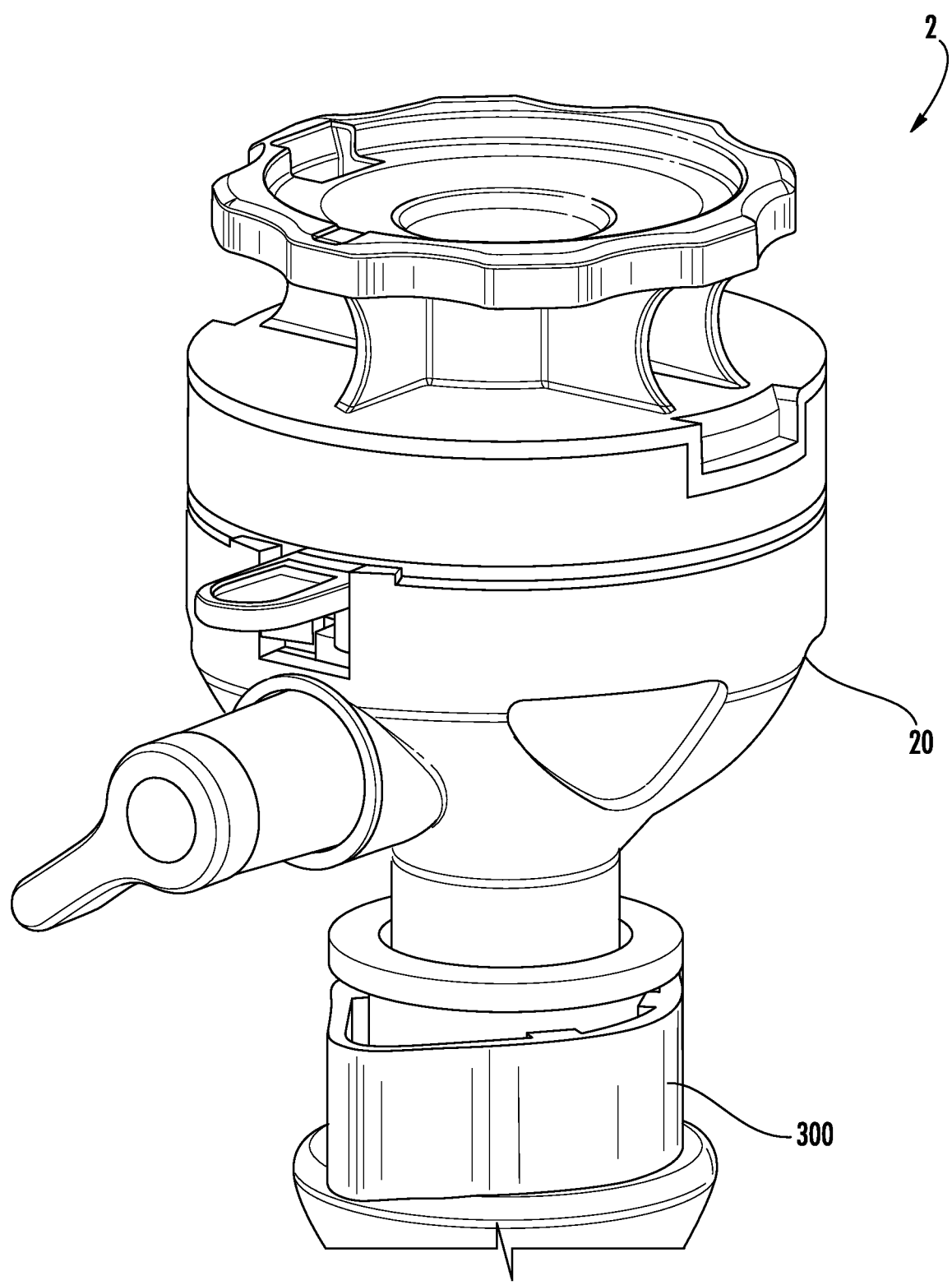
FIG. 13 is a perspective view of the surgical access system of FIG. 12 with the collar thereof positioned at a second axial location along the surgical access device thereof.

In use, the spring 120 of the collar 100 is pivotable between uncompressed (FIG. 6) and compressed (FIG. 7) states to manipulate the annular body 110 of the collar 100 and selectively expose the central passage 110h of the annular body 110 in a lateral direction via separation of the vertical slit 110e of the annular body 110. More specifically, as illustrated by arrows "B" in FIG. 7, the trailing ends 122b, 124b of the spring 120, which may act as grips or handles, are compressed/pivoted from an uncompressed state (FIG. 6) toward a one another against a biasing force imparted by the connecting segment 126 of the spring 120 to separate the leading ends 122a, 122b of the spring 120, as illustrated by arrows "C." As the leading ends 122a, 122b of the first and second arms 122, 124 of the spring 120 separate, the leading ends 122a, 122b of the first and second arms 122, 124 engage the first and second hook members 114d, 114e, of the tubular portion 114, respectively, to separate the pair of opposed end faces 110f, 110g of the annular body 110 and enlarge a width of the vertical slit 110e of the annular body 110 and laterally expose the central passage 110h of the annular body 110 (see FIG. 11 illustrating an alternate embodiment of a collar, described in greater detail below, with a central passage thereof laterally exposed). In particular, while the spring 120 of the collar 100 is disposed in the uncompressed state, the annular body 110 of the collar 100 is disposed in a closed or first condition (e.g., O-shape), and while the spring 120 is disposed in the compressed state, the annular body 110 is disposed in an open or second condition (e.g., C-shape).

In this regard, manipulation of the collar 100 and/or components thereof, enable the collar 100 to be selectively attached to, removed from, and/or repositioned along the cannula 14 of the surgical access device 10 at any suitable axial location therealong. While the collar 110 may be laterally coupled/attached to the cannula 14 of the surgical access device 10, the collar 110 may likewise be axially slid (see arrows "D" in FIG. 1) along the cannula 14 for attaching, detaching, or repositioning of the collar 110 relative to the cannula 14. Additionally, or alternatively, the surgical access device 10 may be moved relative to the collar 100 in likewise fashion as desired by a clinician.

With reference to FIGS. 8-11, one embodiment of a collar 200 includes an annular body 110 and a spring 220 coupled to the annular body 110. The spring 220 of the collar 200 is similar to the spring 120 of the collar 100 and includes first and second arms 222, 224 that are pivotally coupled by a connecting segment 226 of the spring 220. The first arm 222 of the spring 220 includes a first restraining member 222a that extends from the first arm 222 and towards the second arm 224 of the spring 220. The second arm 224 includes a second restraining member 224 that extends from the second arm 224 and towards the first arm 222. The first and second restraining members 222a, 224a of respective first and second arms 222, 224 extend transverse to and/or perpendicular to its respective arm 222, 224. The first and second restraining members 222a, 224a of respective first and second arms 222, 224 are selectively engagable with one another as the first and second arms 222, 224 are compressed toward one another to prevent over-compression of the first and second arms 222a, 224a. Prevention of over-compression helps reduce stress/strain on the spring 220 and prolong lifespan of the spring 220 and the collar 200.

Turning now to FIGS. 12-19, another embodiment of a surgical access system, generally referred to as surgical access system 2, includes a surgical access device 20 and a collar 300 that is selectively mountable to the surgical access device 20. The surgical access device 20 is similar to the surgical access device 10 of surgical access system 1 and generally includes a housing 22 that supports a seal assembly 22a and a cannula or trocar 24 that extends distally from the housing 22.

Figure 14:
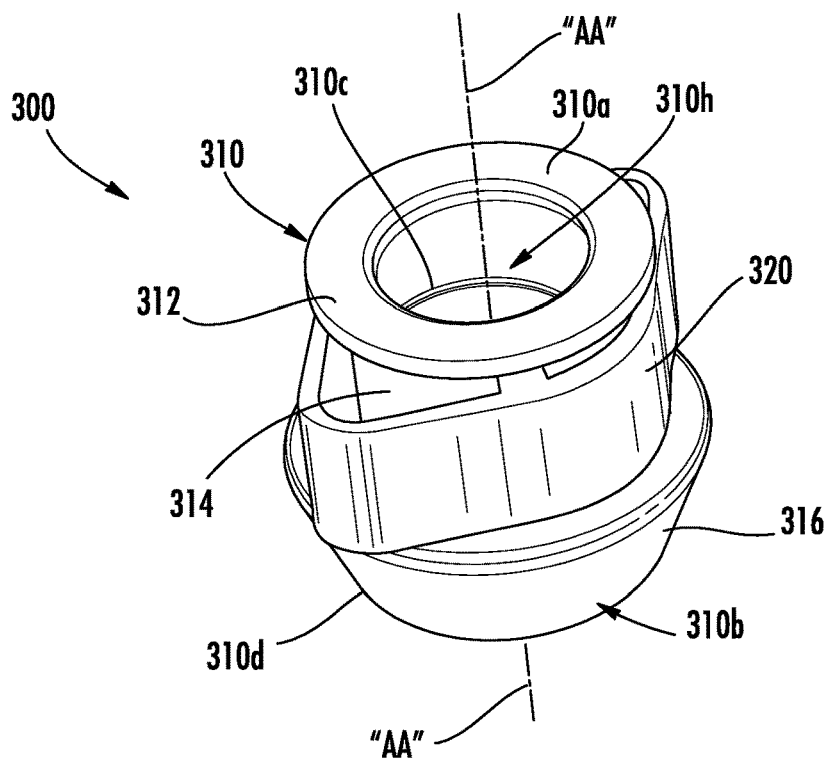
FIG. 14 is a perspective view of the collar of the surgical access system of FIGS. 12 and 13.
Figure 15:
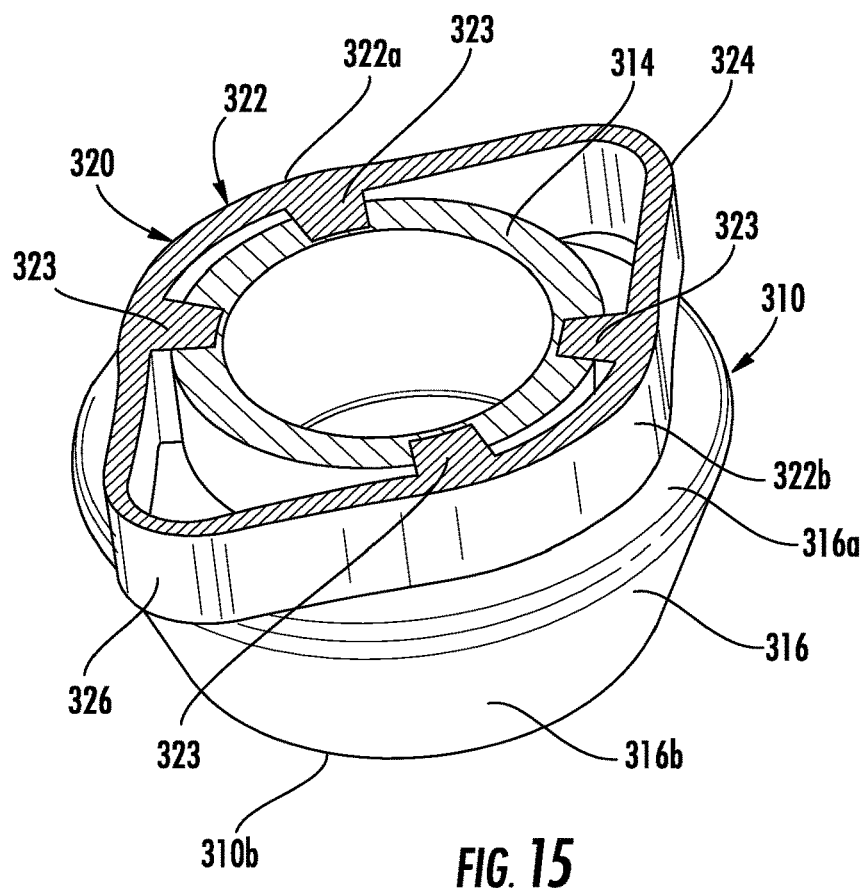
FIG. 15 is a perspective view of the collar of FIG. 14 with a top portion thereof removed for clarity.
Figure 16:
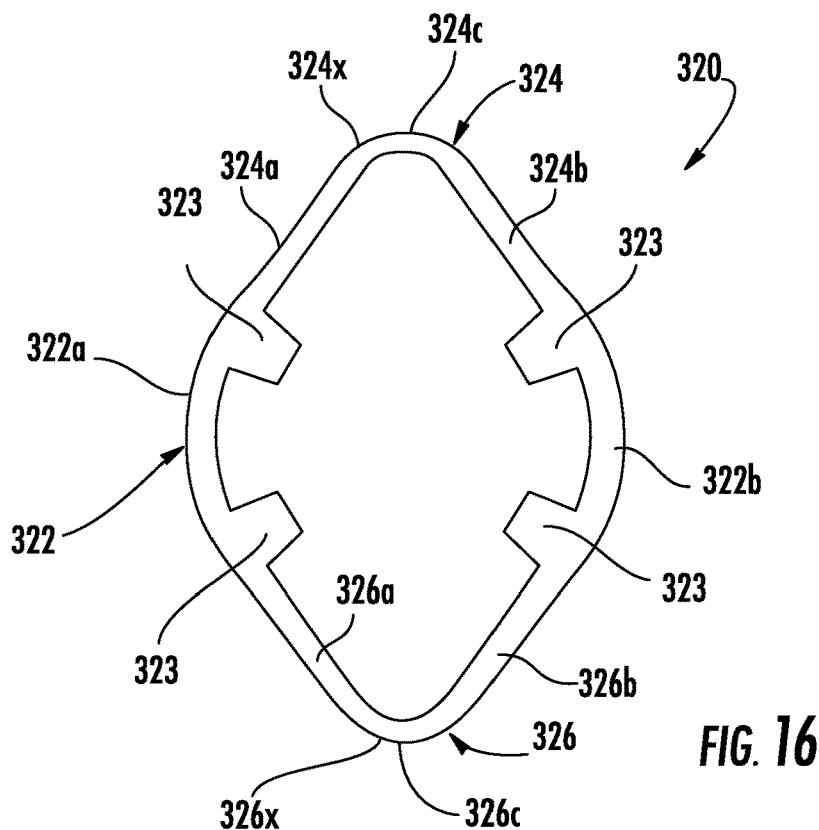
FIGS. 16 and 17 are progressive views of a spring of the collar of FIG. 14, the spring shown positioned in uncompressed and compressed states.
Figure 17:
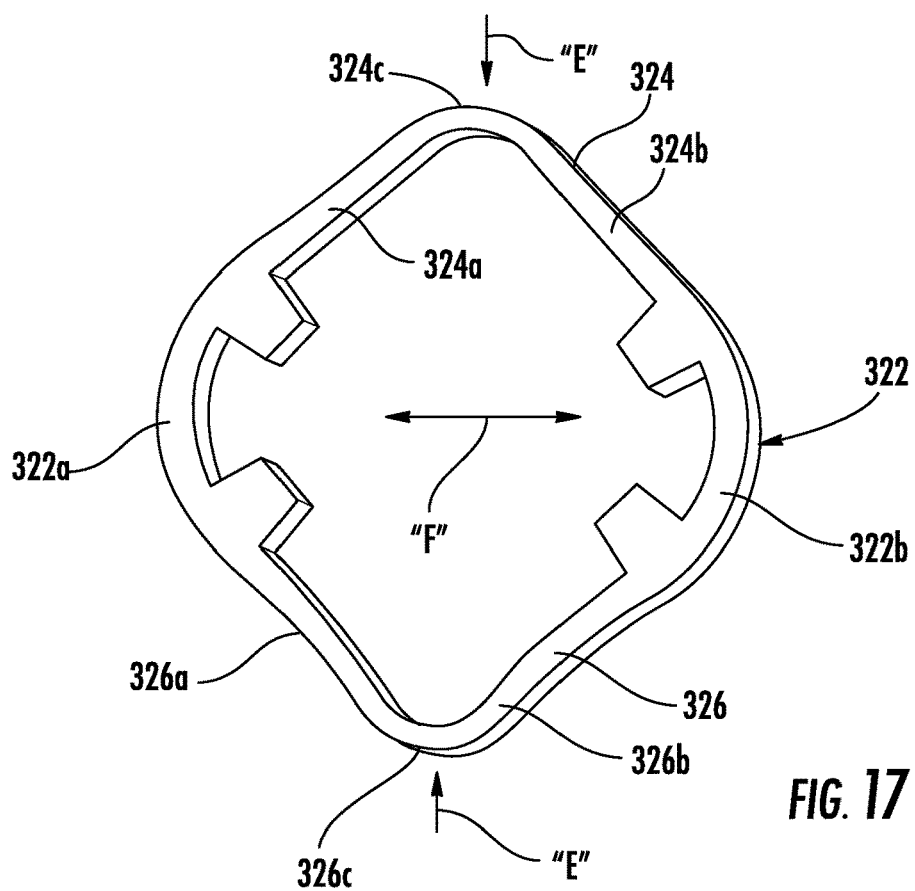
Figure 18:
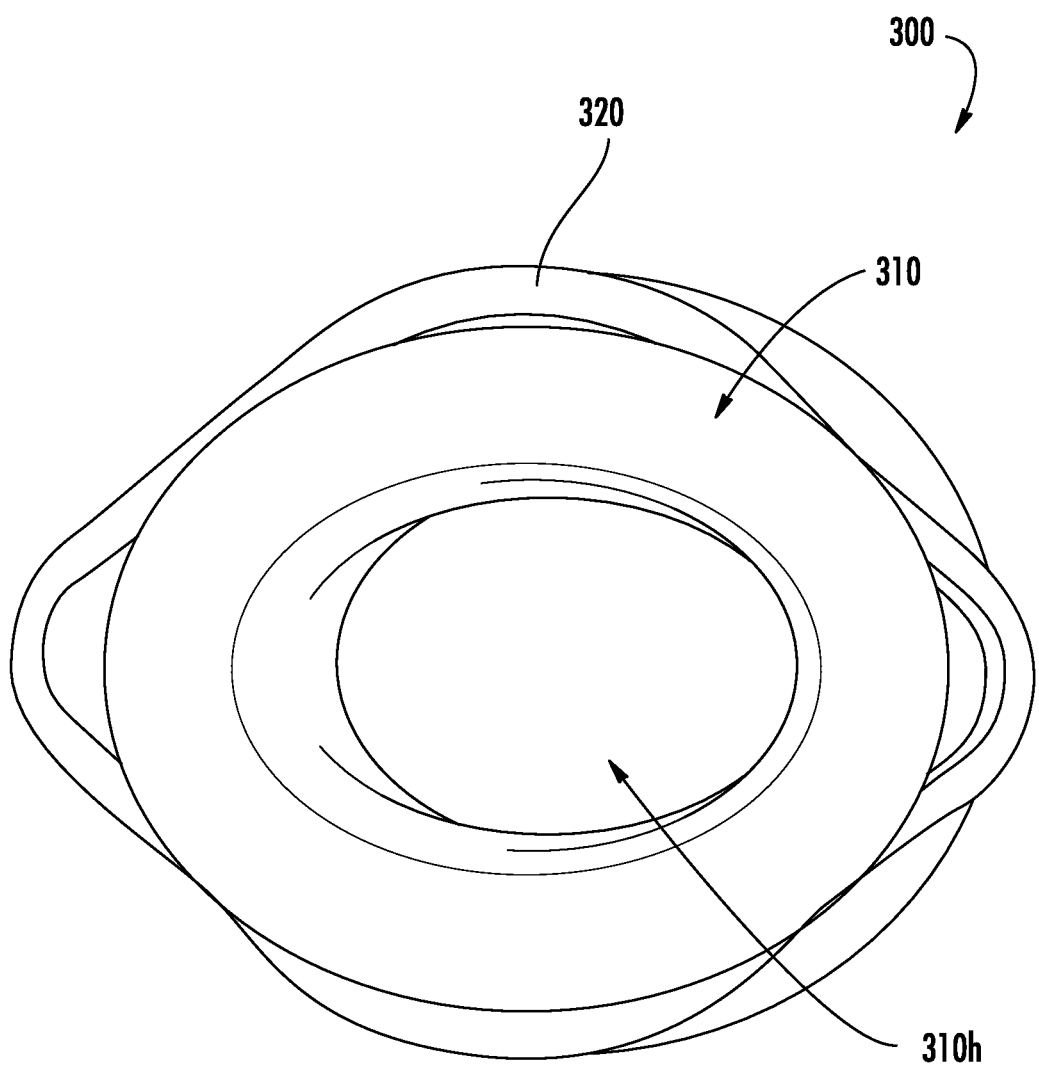
FIGS. 18 and 19 are progressive views of the collar of FIG. 14, the collar shown positioned in uncompressed and compressed states.
Figure 19:
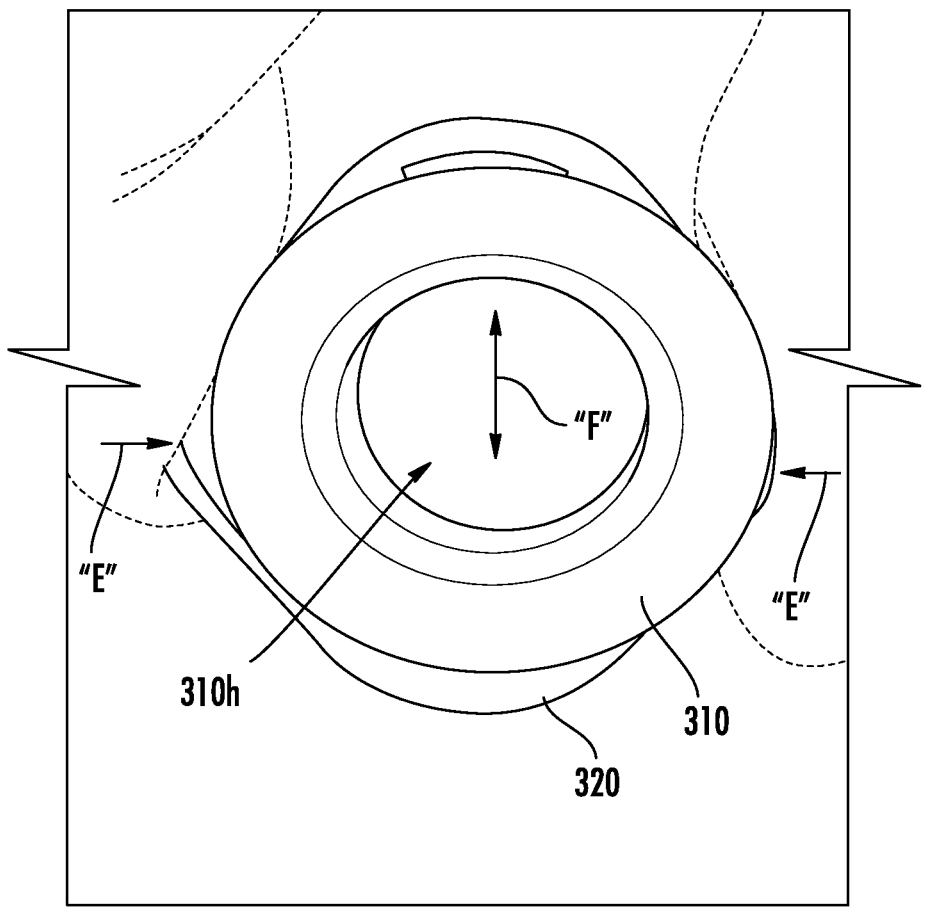

With reference to FIGS. 14 and 15, the collar 300 of the surgical access system 2 includes an annular body 310 and spring 320 coupled to the annular body 310. The annular body 310 of the collar 300 has a proximal end 310a and a distal end 310b. The annular body 310 has an inner surface 310c and an outer surface 310d. The inner surface 310c of the annular body 310 defines a central passage 310h through the annular body 310. The central passage 310h of the annular body 310 extends from the proximal end 310a of the annular body 310 to the distal end 310b of the annular body 310 along a central longitudinal axis "AA" of the annular body 310. The annular body 310 includes a flange 312 on the proximal end 310a of the annular body 310. The flange 312 is supported on a proximal end of a tubular portion 314 of the annular body 310.

The tubular portion 314 of the annular body 310 extends distally from the flange 312 to a distal portion 316 of the annular body 310. Similar to the tubular portion 114 of the annular body 110 of the collar 100, the tubular portion 314 of the annular body 310 of the collar 300 may include any number of diameters, which may be the same as, or different from, one or more of the other diameters. In certain embodiments, the tubular portion 314 may include a transition portion (not shown) similar to the tubular portion 114 of the collar 100. In some embodiments, the tubular portion 314 of the annular body 310 may include a single diameter therealong.

The distal portion 316 of the annular body 310 includes a ledge 316a and a tapered portion 316b that tapers distally from the ledge 316a to the distal end 310b of the annular body 310 similar to the distal portion 116 of the collar 100 (see FIG. 4).

The spring 320 of the collar 300 is supported about the tubular portion 314 of the annular body 310 between a bottom surface of the flange 312 and a top surface of the ledge 316a of the distal portion 316 of the annular body 310. The spring 320 of the collar 300 includes a mounting portion 322 having first and second segments 322a, 322b. The first and second segments 322a, 322b of the mounting portion 322 are supported on opposite sides of the tubular portion 314 of the annular body 310. The mounting portion 322 of the spring 320 includes tabs 323 that extend from the first and second segments 322a, 322b of the mounting portion 322 to the tubular portion 314 of the annular body 310. In some embodiments, the tabs 323 of the mounting portion 322 may be integrally formed with the mounting portion 322 and/or the tubular portion 314 of the annular body 310. In some embodiments, the tabs 323 may be secured to the mounting portion 322 and/or tubular portion 314 using any suitable fastening technique (e.g., ultrasonic welding, adhesive, friction fit, etc.).

The spring 320 of the collar 300 further includes first and second flexible portions 324, 326 that extend from opposite sides of the mounting portion 322 of the spring 320 to respective free ends 324x, 326x (FIGS. 16 and 17) of the first and second flexible portions 324, 326. In some embodiments, the spring 320 may include an elliptical or substantially elliptical configuration. The first flexible portion 324 of the spring 320 includes first and second fingers 324a, 324b and the second flexible portion 326 of the spring 320 includes first and second fingers 326a, 326b. The first segment 322a of the mounting portion 322 connects the first fingers 324a, 326a of the respective flexible portions 324, 326 of the spring 320 and the second segment 322b of the mounting portion 322 connects the second fingers 324b, 326b of the respective flexible portions 324, 326 of the spring 320. The first and second fingers 324a, 324b of the first flexible portion 324 are connected together at a vertex 324c disposed at the free end 324x of the first flexible portion 324. Similarly, the first and second fingers 326a, 326b of the second flexible portion 326 are connected together at a vertex 326c disposed at the free end 326x of the second flexible portion 326.

In use, with reference to FIGS. 12-19, the spring 320 of the collar 300 is movable between uncompressed (FIGS. 14, 16, and 18) and compressed (FIGS. 17, 19) states to manipulate the annular body 310 and enlarge the central passage 310h of the annular body 310. More specifically, compression of the vertices 324c, 326c of the spring 320 toward one another, as illustrated by arrows "E" in FIGS. 11, 17 and 19 (e.g., toward the longitudinal axis "AA" of the collar 300), causes the first and second fingers 324a, 326a, 324b, 326b of the respective first and second flexible portions 324, 326 of the spring 320 to pivot outwardly so that the first and second segments 322a, 322b of the mounting portion 322 separate further from one another, as illustrated by arrows "F" in FIGS. 11, 17 and 19 (e.g., away from the longitudinal axis "AA" of the collar 300). As the first and second segments 322a, 322b of the mounting portion 322 separate from one another, the tabs 323 of the mounting portion 322 draw the tubular portion 314 of the annular body 310 outwardly to enlarge the central passage 310h of the annular body 310. With the central passage 310h of the annular body 310 disposed in an enlarged condition, the collar 300 can be moved axially (e.g., relative to a longitudinal axis "XX" of the surgical access device 20) along the cannula 24 of the surgical access device 20, as indicated by arrows "D" (see FIG. 12). Alternatively, and or additionally, the surgical access device 20 can be moved axially relative to the collar 300 while the central passage 310h of the annular body 310 is disposed in an enlarged condition.

The spring 320 of the collar 300 is biased toward its initial or uncompressed state, whereby removal of the compression forces from the vertices 324c, 326c of the spring 320 causes the first and second fingers 324a, 326a, 324b, 326b of the respective first and second flexible portions 324, 326 to pivot inwardly so that the first and second segments 322a, 322b of the mounting portion 322 approximate toward one another (e.g., toward the longitudinal axis "AA" of the collar 300). As the first and second segments 322a, 322b of the mounting portion 322 move toward one another, the tabs 323 of the mounting portion 322 drive the tubular portion 314 of the annular body 310 inwardly to shrink the central passage 310h toward the longitudinal axis "AA" of the collar 300 and enable the inner surfaces 310c of the annular body 310 to secure to an outer surface of the cannula 24 of the surgical access device 20 (e.g., friction-fit).

In this regard, manipulation of the collar 300 and/or components thereof between uncompressed and compressed states enable the collar 300 to be selectively axially slid along the cannula 24 of the surgical access device 20 for selective attachment to, removal from, and/or repositioning along the cannula 24 of the surgical access device 20. Additionally, or alternatively, the surgical access device 20 may be selectively moved relative to the collar 300 in likewise fashion as desired by a clinician.

Any of the presently disclosed embodiments and/or components thereof may be formed of any suitable material. For example, any of the presently disclosed embodiments and/or components thereof may be formed, at least partially, of a flexible polymeric material such as soft rubber.

The various embodiments disclosed herein may also be configured to work with robotic surgical systems and what is commonly referred to as "Telesurgery." Such systems employ various robotic elements to assist the clinician and allow remote operation (or partial remote operation) of surgical instrumentation. Various robotic arms, gears, cams, pulleys, electric and mechanical motors, etc. may be employed for this purpose and may be designed with a robotic surgical system to assist the clinician during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of clinicians or nurses may prep the patient for surgery and configure the robotic surgical system with one or more of the instruments disclosed herein while another clinician (or group of clinicians) remotely control the instruments via the robotic surgical system. As can be appreciated, a highly skilled clinician may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the clinician to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the clinician. The scale factor or gearing ratio may be adjustable so that the operator can control the resolution of the working ends of the surgical instrument(s).

The master handles may include various sensors to provide feedback to the clinician relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the clinician with enhanced tactile feedback simulating actual operating conditions. The master handles may also include a variety of different actuators for delicate tissue manipulation or treatment further enhancing the clinician's ability to mimic actual operating conditions.

Figure 20:
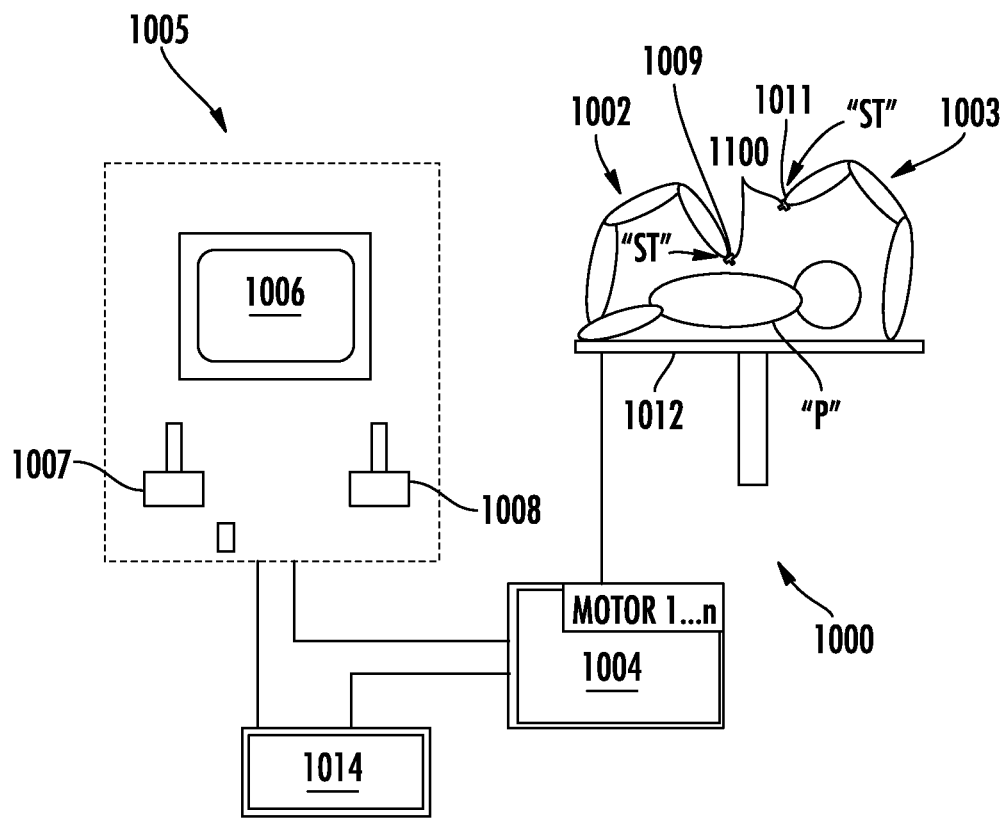
FIG. 20 is a schematic illustration of a medical work station and operating console in accordance with the present disclosure.

Referring also to FIG. 20, a medical work station is shown generally as work station 1000 and generally may include a plurality of robot arms 1002, 1003; a control device 1004; and an operating console 1005 coupled with the control device 1004. The operating console 1005 may include a display device 1006, which may be set up in particular to display three-dimensional images; and manual input devices 1007, 1008, by means of which a person (not shown), for example a clinician, may be able to telemanipulate the robot arms 1002, 1003 in a first operating mode.

Each of the robot arms 1002, 1003 may include a plurality of members, which are connected through joints, and an attaching device 1009, 1011, to which may be attached, for example, a surgical tool "ST" supporting an end effector 1100 (e.g., a pair of jaw members) or surgical access system, in accordance with any one of several embodiments disclosed herein, as will be described in greater detail below.

The robot arms 1002, 1003 may be driven by electric drives (not shown) that are connected to the control device 1004. The control device 1004 (e.g., a computer) may be set up to activate the drives, in particular by means of a computer program, in such a way that the robot arms 1002, 1003, their attaching devices 1009, 1011 and thus the surgical tool (including the end effector 1100) and/or surgical access system execute a desired movement according to a movement defined by means of the manual input devices 1007, 1008. The control device 1004 may also be set up in such a way that it regulates the movement of the robot arms 1002, 1003 and/or of the drives.

The medical work station 1000 may be configured for use on a patient "P" lying on a patient table 1012 to be treated in a minimally invasive manner by means of the end effector 1100. The medical work station 1000 may also include more than two robot arms 1002, 1003, the additional robot arms likewise connected to the control device 1004 and telemanipulatable by means of the operating console 1005. A surgical systems, such as the presently disclosed surgical access systems, or a surgical tool (including an end effector 1100) may also be attached to the additional robot arm. The medical work station 1000 may include a database 1014 coupled with the control device 1004. In some embodiments, pre-operative data from patient/living being "P" and/or anatomical atlases may be stored in the database 1014.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what is particularly shown and described.

What is claimed is:

1. A surgical access system, comprising:
a surgical access device including:
a housing; and
a cannula extending from the housing; and
a collar including:
an annular body mounted to the cannula, the annular body including an annular flange on a proximal end thereof and a tubular portion that extends distally from the annular flange, the annular body defining a longitudinal axis; and
a spring supported within the tubular portion of the annular body, the spring including a first flexible portion and a second flexible portion that are coupled together by a first segment and a second segment, the first and second flexible portions movable relative to one another to move the first and second segments relative to one another to selectively fix the annular body at predetermined locations along the cannula, the spring having a tab, the tab supported within and secured to the tubular portion of the annular body such that the tab draws the tubular portion outwardly as the tab moves away from the longitudinal axis.

2. The surgical access system of claim 1, wherein movement of the first and second flexible portions toward one another causes the first and second segments to move away from one another.

3. The surgical access system of claim 2, wherein movement of the first and second flexible portions away from one another causes the first and second segments to move toward one another.

4. The surgical access system of claim 1, wherein the annular body defines a central passage therethrough, and wherein movement of the spring between an uncompressed state and a compressed state changes a diameter of the central opening.

5. The surgical access system of claim 4, wherein when the spring is in an uncompressed state, the central passage is arranged to enable the annular body to frictionally secure to an outer surface of the cannula.

6. The surgical access system of claim 1, wherein the annular body includes a tapered distal portion that extends distally from the tubular portion.

7. The surgical access system of claim 6, wherein each of the first and second segments includes at least one tab that is coupled to the tubular portion.

8. The surgical access system of claim 6, wherein the tapered distal portion extends distally from a ledge, the spring positioned proximal to the ledge.

9. The surgical access system of claim 1, wherein the spring has a substantially elliptical configuration.

10. The surgical access system of claim 1, wherein each of the first and second flexible portions includes first and second fingers that are coupled together at a vertex.

11. A collar for a surgical access device, the collar comprising:
an annular body including a flange on a proximal end thereof and a tubular portion that extends distally from the flange, the annular body defining a longitudinal axis; and
a spring supported within the tubular portion of the annular body such that the tubular portion and the spring move together, the spring including a first flexible portion and a second flexible portion that are coupled together by a first segment and a second segment, the first and second flexible portions movable relative to one another to move the first and second segments relative to one another to selectively fix the annular body at predetermined locations along the surgical access device, the spring having a tab, the tab supported within and secured to the tubular portion of the annular body such that the tab draws the tubular portion outwardly as the tab moves away from the longitudinal axis.

12. The collar of claim 11, wherein movement of the first and second flexible portions toward one another causes the first and second segments to move away from one another.

13. The collar of claim 12, wherein movement of the first and second flexible portions away from one another causes the first and second segments to move toward one another.

14. The collar of claim 11, wherein the annular body defines a central passage therethrough, and wherein movement of the spring between an uncompressed state and a compressed state changes a diameter of the central opening.

15. The collar of claim 14, wherein when the spring is in an uncompressed state, the central passage is arranged to enable the annular body to frictionally secure to an outer surface of a cannula of the surgical access device.

16. The collar of claim 11, wherein the annular body includes a tapered distal portion that extends distally from the tubular portion.

17. The collar of claim 16, wherein each of the first and second segments includes at least one tab that is coupled to the tubular portion.

18. The collar of claim 16, wherein the tapered distal portion extends distally from a ledge, the spring positioned proximal to the ledge.

19. The collar of claim 11, wherein the spring has a substantially elliptical configuration.

20. A collar for a surgical access device, the collar comprising:
an annular body defining a central passage and a longitudinal axis therethrough and including a tubular portion and a flange, the flange disposed proximal to the tubular portion, the annular body further including a tapered distal portion that extends distally from the tubular portion; and
a spring including a mounting portion that is secured within the tubular portion, the mounting portion including a first flexible portion and a second flexible that are movable relative to one another to change a diameter of the central passage of the annular body for selectively fixing the annular body at predetermined locations along the surgical access device, the spring having a tab, the tab supported within and secured to the tubular portion of the annular body such that the tab draws the tubular portion outwardly as the tab moves away from the longitudinal axis.

* * * * *